United States Patent [19]

Yamamuro et al.

[11] Patent Number: 4,458,010

[45] Date of Patent: Jul. 3, 1984

[54] PROCESS FOR BLEACHING COLOR PHOTOGRAPHIC SENSITIVE MATERIALS

[75] Inventors: Kiyohiko Yamamuro; Shigeo Hirano, Yasno Iwasa, all of Kanagawa, Japan

[73] Assignee: Fuji Photo Film Co., Ltd., Kanagawa, Japan

[21] Appl. No.: 441,207

[22] Filed: Nov. 12, 1982

[30] Foreign Application Priority Data

Nov. 13, 1981 [JP] Japan ............................ 56-181994

[51] Int. Cl.[3] ............................................ G03C 7/00

[52] U.S. Cl. .................................. 430/393; 430/429; 430/430; 430/455; 430/461; 430/566; 430/611

[58] Field of Search ............... 430/393, 429, 455, 430, 430/461, 611, 566

[56] References Cited

U.S. PATENT DOCUMENTS

| | | | |
|---|---|---|---|
| 3,647,469 | 3/1972 | Huckstadt et al. | 430/611 |
| 3,772,020 | 11/1973 | Smith | 430/393 |
| 3,893,858 | 7/1975 | Wabnitz | 430/393 |
| 4,163,669 | 8/1979 | Kanada et al. | 430/393 |
| 4,292,401 | 9/1981 | Itoh et al. | 430/393 |
| 4,293,639 | 10/1981 | Itoh et al. | 430/393 |

*Primary Examiner*—J. Travis Brown

*Attorney, Agent, or Firm*—Sughrue, Mion, Zinn, Macpeak & Seas

[57] ABSTRACT

A process for bleaching color photographic sensitive materials and color photographic sensitive materials are disclosed. The process comprises bleaching the silver halide color photographic sensitive materials which are comprised of a support base, a silver halide emulsion layer, and a compound represented by the general formula (I) or strong acid salts thereof in a layer which does not substantially form silver salts of said compounds with a treating solution containing persulfate after being exposed to the light and carrying out color development:

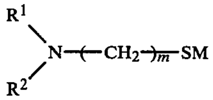

(I)

wherein M represents a hydrogen atom, an alkali metal atom, an alkaline earth metal, a quaternary ammonium group, a quaternary phosphonium group, an amidino group or

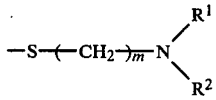

, $R^1$ and $R^2$ each represents a hydrogen atom or an aliphatic group, and m represents an integer of 2 to 4. The bleaching process effectively bleaches color sensitive materials having a high silver content and/or a colloidal silver layer without creating a bad odor.

18 Claims, No Drawings

PROCESS FOR BLEACHING COLOR PHOTOGRAPHIC SENSITIVE MATERIALS

FIELD OF THE INVENTION

The present invention relates to a process for bleaching silver halide color photographic sensitive materials (hereinafter, referred to as color sensitive material) and, particularly, to a process for bleaching color sensitive materials having an improved bleaching property with persulfate.

BACKGROUND OF THE INVENTION

Generally, basic processing steps for processing silver halide color photographic sensitive materials are the color development step and the desilvering step. More specifically, in the color development step, silver halide in the exposed silver halide color photographic material is reduced by a color developing agent to form silver and the oxidized color developing agent reacts with couplers to form dye images. Thereafter, the color sensitive material is treated in the desilvering step, where silver formed in the prior step is oxidized by the action of an oxidizing agent (which is generally called a bleaching agent). The oxidized silver is then removed from the photographic material by dissolution with a complexing agent for silver ions called a fixing agent. Thus, only dye images can be formed on the photographic material. The practical development processing includes supplementary steps for maintaining the photographic and physical quality of images or for improving preservation stability of images to an extent beyond that possible with the above-described two basic steps of color development and desilvering. For example, it is possible to use a hardening bath to prevent excessive softening of the sensitive layer during processing, a stopping bath for effectively stopping the development reaction, an image stabilizing bath for stabilizing the images, or a defilming bath for removing a backing layer of the base, etc.

There are two variations of the above-described desilvering step. In accordance with one, the processing is carried out in one stage using a bleach-fixing bath containing a bleaching agent and a fixing agent. In accordance with the other, the processing is carried out in two stages of bleaching and fixing using different baths.

Examples of useful bleaching agents for the bleaching solution include ferricyanides, potassium bichromate, ferric ion complex salts and persulfates. A bleaching solution containing ferricyanides has been found to have a particularly excellent bleaching function. However, ferricyan ions and ferrocyan ions exhausted by overflowing during the processing or placement in the washing water after bleaching are subjected to photochemical oxidation and thus form cyan compounds which have high toxicity and cause injury. Accordingly, it is desired to develop a bleaching agent which takes the place of ferricyanides.

Ferric ion complex salts are sometimes used as bleaching agents in a bleach-fixing solution for color printing paper. (German Pat. Nos. 866,605 and 966,410, and British Pat. Nos. 746,567, 933,008 and 1,014,396.) However, since the bleaching solution or the bleach-fixing solution containing ferric ion complex salts has a poor oxidation ability, a long period of time is required for processing when using color sensitive photographic materials which include silver iodobromide having a high concentration of silver halide.

In any case, bleach processing with the use of metal ions such as those of ferricyanides or ferric ion complex salts cause pollution of water liquor. Accordingly, processes which do not use metal ions, for example, persulfate bleaching processes, are more suitable. However, the persulfate bleaching bath is not desirable because it has weaker bleaching ability than ferric ion complex salts and the bleaching requires a very long period of time. Therefore, when using color sensitive materials with photographic sensitivity which contains a large amount of silver halide, it would be desirable to develop new techniques for promoting the persulfate bleaching.

Examples of processes for promoting bleaching with persulfates include processes which involve adding amino compounds described in, for example, U.S. Pat. Nos. 3,772,020 and 3,893,858 and *Research Disclosure*, No. 15704, etc., to treating solutions (a bleaching bath, a bleach-fixing bath or a previous bath thereof).

However, these processes also require a fairly long period of time to sufficiently carry out bleaching. Further, since many of the above-described amino compounds give out a bad smell, it is not desirable to add them to treating solutions.

Further, according to these processes, it is difficult to sufficiently bleach color sensitive materials having a high silver content which have colloidal silver layers such as a yellow filter layer or an antihalation layer, etc., while preventing an increase in fogs caused by said colloidal silver during preservation.

SUMMARY OF THE INVENTION

A primary object of the present invention is to provide a process for bleaching color sensitive materials having improved bleaching ability using persulfates. Another object is to provide a process for bleaching color sensitive materials having improved bleaching ability using persulfates, which does not give out a bad smell. Yet another object is to provide a bleaching process using persulfates, by which color sensitive materials having a high silver content can be effectively bleached. Still another object is to provide a bleaching process using persulfates, by which color sensitive materials having a colloidal silver layer can be effectively bleached.

These and other objects of the present invention have been attained by a process for bleaching color sensitive materials which comprises bleaching a color sensitive material containing at least one of compounds represented by the general formula (I) or strong acid salts thereof in a layer which does not substantially form silver salts of said compounds with a treating solution containing persulfate after exposure to light and carrying out color development.

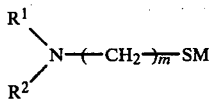
(I)

wherein M represents a hydrogen atom, an alkali metal atom (lithium, sodium or potassium, etc.) an alkaline earth metal (calcium or magnesium, etc.), a quaternary ammonium group (preferably, $NH_4^{\oplus}$ or that having 4 to 30 carbon atoms, for example, $(CH_3)_4N^{\oplus}$, $(C_2H_5)_4N^{\oplus}$, $(C_4H_9)_4N^{\oplus}$, $C_6H_5CH_2N^{\oplus}(CH_3)_3$ or $C_{16}H_{33}N^{\oplus}(CH_3)_3$, etc.), a quaternary phosphonium group (preferably, that having 4 to 30 carbon atoms, for example, $(C_4H_9)_4P^{\oplus}$, $C_{16}H_{33}P^{\oplus}(CH_3)_3$ or $C_6H_5CH_2P^{\oplus}(CH_3)_3$, etc.), an amidino group or

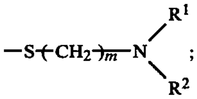
;

$R^1$ and $R^2$ each represents a hydrogen atom or an aliphatic group, preferably, an aliphatic group having 1 to 30 carbon atoms, for example, an alkyl group or an alkenyl group, and, particularly, an alkyl group having 1 to 5 carbon atoms; and m represents an integer of 2 to 4.

DETAILED DESCRIPTION OF THE INVENTION

Examples of strong acid salts of compounds represented by the general formula (I) include hydrochlorides, sulfates, p-toluenesulfonates and methanesulfonates.

In the following, preferred examples of the compounds represented by the general formula (I) are described.

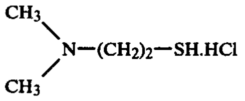
(I)-(1)

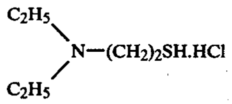
(I)-(2)

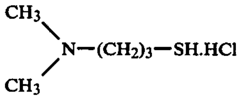
(I)-(3)

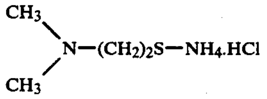
(I)-(4)

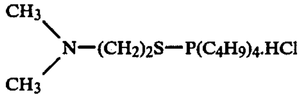
(I)-(5)

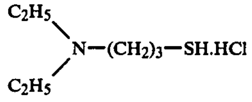
(I)-(6)

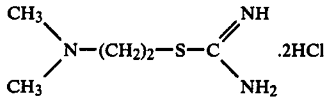
(I)-(7)

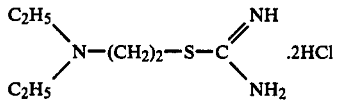
(I)-(8)

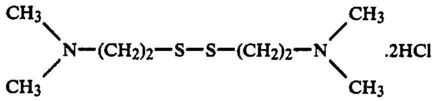
(I)-(9)

-continued

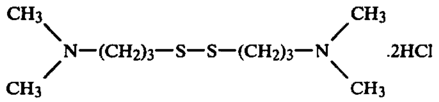
(I)-(10)

These compounds are known and can be synthesized by, for example, the following synthesis passage:

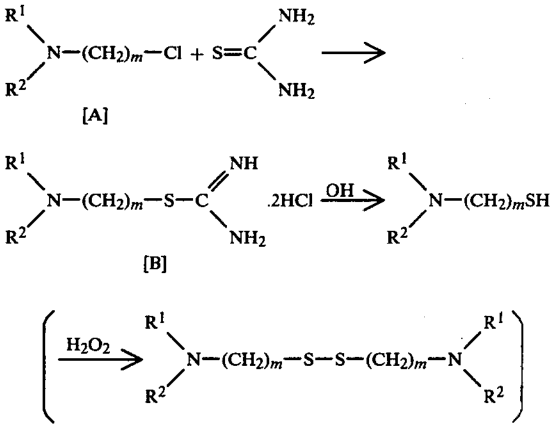

wherein $R^1$, $R^2$ and m represent the same meaning as in the general formula (I).

Compounds represented by the general formula (I) wherein M represents an amidino group are obtained by refluxing active chloride [A] and a solution of thiourea in alcohol (for example, n-ubtanol) with heating. ([B])

Compounds wherein M represents a hydrogen are obtained by hydrolyzing the compound [B].

Compounds wherein M represents the group excepting the above-described groups are obtained by substituting with M when hydrolyzing the compound [B] to form salts of a mercapto group, or by oxidation.

The compounds represented by the general formula (I) of the present invention are added to at least one of layers which do not form substantially silver salts in the color sensitive material. Although the amount to be added is not restricted, it is generally preferred to be in a range of $1\times10^{-7}$ mol to $1\times10^{-3}$ mol and, preferably $1\times10^{-6}$ mol to $1\times10^{-4}$ mol based on 1 $m^2$.

Since the color sensitive materials used for the bleaching process of the present invention are those which can be used for various uses (for example, color positive, color paper, color negative and color reversal materials (containing or not containing couplers), etc., and, particularly, high silver content color sensitive materials having a total silver content of 30 mg/100 $cm^2$ or more and, particularly, 40 mg/100 $cm^2$ or more), they may have various layer constructions depending on each use. An example of a layer construction capable of particularly exhibiting the effect of the present invention includes a construction prepared by applying a colloidal silver antihalation layer, (an intermediate layer), a red-sensitive layer, (an intermediate layer), a green-sensitive layer, a colloidal silver yellow filter layer, a blue-sensitive layer and a protective layer to a base in that order. The layer described in the parenthesis may be omitted. The above-described red-sensitive layer, green-sensitive layer and blue-sensitive layer may be composed of a low-speed layer and a high-speed layer, respectively. Other examples of useful layer constructions include one wherein at least one of a red-sensitive layer, a green-sensitive layer and a blue-sensitive layer is composed of three layer parts as described in Japanese Patent Publication No. 15495/74 (corresponding to U.S. Pat. No. 3,843,369), a layer construction composed of high-speed emulsion layer units and low-speed emulsion layer units as described in Japanese Patent Application (OPI) No. 49027/76 (the term "OPI" as used herein refers to a "published unexamined Japanese patent application") and layer construction described in German Patent Application (OLS) Nos. 2,622,922, 2,622,923, 2,622,924, 2,704,826 and 2,704,797 (incorporated herein by reference to disclose such layer construction).

In the above-described color sensitive materials, the compound represented by the general formula (I) of the present invention are added to layers where silver salts of said compounds are not formed, preferably, layers which do not contain silver halide such as a protective layer, a subbing layer, an intermediate layer, a yellow filter layer or an antihalation layer, etc. Particularly, it is preferred to add the compound of general formula (I) to layers containing colloidal silver. It is particularly advantageous to add the compound of general formula (I) to a colloidal silver antihalation layer which is the most difficult to bleach, because the bleaching efficiency of said layer becomes very high.

In order to effectively carry out the bleaching with persulfate, it is preferred as an embodiment of the present invention to use compounds represented by the following general formula (II) together with the compounds represented by the general formula (I). The compounds represented by the general formula (II) have a function of preventing variation of photographic properties of the color sensitive materials during preservation and, particularly, preventing increase of fogs caused by colloidal silver. While other compounds having the same function, which are called stabilizing agents or antifogging agents, are often highly adsorptive on silver to prevent desilvering, the compounds represented by the general formula (II) do not prevent desilvering. Accordingly, it is very advantageous to use them together with the compounds represented by the general formula (I) of the present invention.

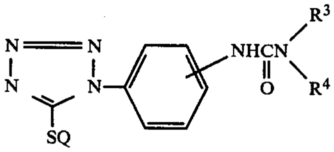

(II)

In the formula, Q represents a hydrogen atom, an alkali metal atom or a quaternary ammonium group. $R^3$ and $R^4$ each represents a hydrogen atom, a nonsubstituted or substituted aliphatic group or a nonsubstituted or substituted aromatic group. $R^3$ and $R^4$ may be identical or different from each other, and $R^3$ and $R^4$ may form a ring by bonding together.

The compounds of the present invention are described in greater detail in the following. In the general formula (II), examples of alkali metal atoms represented by Q include $Li^{\oplus}$, $Na^{\oplus}$ and $K^{\oplus}$, etc.

Examples of quaternary ammonium groups include $H_4N^{\oplus}$, $(CH_3)_4N^{\oplus}$, $(C_4H_9)_4N^{\oplus}$, n-$C_{12}H_{25}(CH_3)_3N^{\oplus}$, n-$C_{16}H_{33}(CH_3)_3N^{\oplus}$ and $C_6H_5CH_2(CH_3)_3N^{\oplus}$, etc.

Examples of preferable aliphatic groups represented by $R^3$ and $R^4$ include alkyl groups and alkenyl groups having 18 or less carbon atoms. Specifie examples of these preferred groups include a methyl group, an ethyl group, an n-propyl group, an n-butyl group, a t-butyl group, an n-pentyl group, an n-hexyl group, a cyclohexyl group, an n-octyl group, an n-dodecyl group, an n-octadecyl group and an allyl group.

Of the aromatic groups represented by $R^3$ and $R^4$, aryl groups having 6 to 20 carbon atoms are preferred. Examples of them include a phenyl group and a naphthyl group.

The ring formed by $R^3$ and $R^4$ is that which has 2 to 10 carbon atoms and may contain O, N or S in the ring. Examples of groups forming the ring include $-(CH_2)_4-$, $-(CH_2)_5-$, $-(CH_2)_6-$, $-CH_2CH_2OCH_2CH_2-$, and

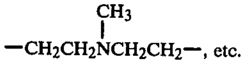

etc.

Examples of substituents in $R^3$ and $R^4$ include alkoxy groups (for example, methoxy group and ethoxy group), halogens (for example, chlorine and bromine, etc.), alkyl groups (for example, methyl group and ethyl group, etc.), a phenyl group, alkoxycarbonyl groups (for example, ethoxycarbonyl group), acyl groups (for example, acetyl group), acyloxy groups (for example, acetyloxy group), a cyano group, a nitro group, alkylthio groups (for example, methylthio group), amido groups (for example, acetamido group) and sulfonamido groups (for example, methanesulfonamido group), etc.

Particularly preferably, at least one of the $R^3$ and $R^4$ represents an alkyl group having 1 to 6 carbon atoms or a phenyl group, and most preferably a methyl group, an ethyl group, an n-propyl group, an n-butyl group or an n-pentyl group.

In the following, examples of the compounds represented by the general formula (II) of the present invention are described, but the present invention is not limited to them.

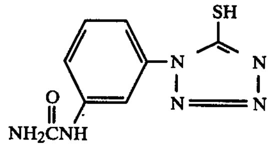

(II)-(1)

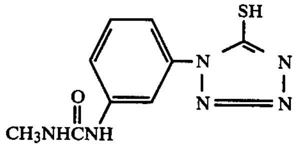

(II)-(2)

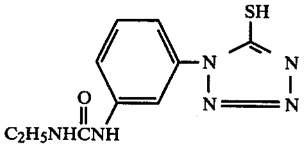

(II)-(3)

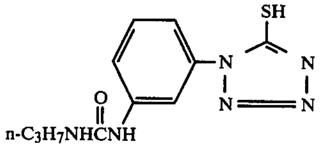

(II)-(4)

-continued
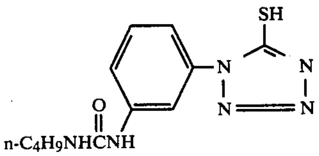
(II)-(5)
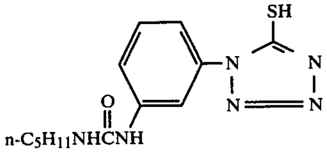
(II)-(6)
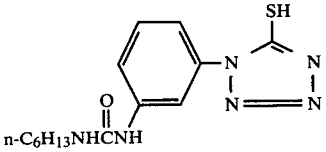
(II)-(7)
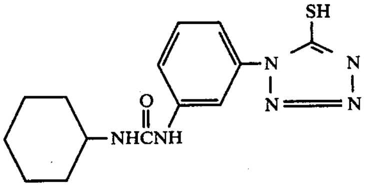
(II)-(8)
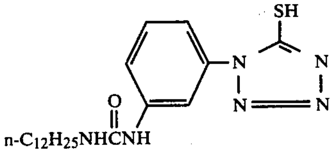
(II)-(9)
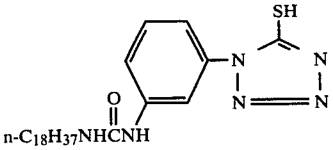
(II)-(10)
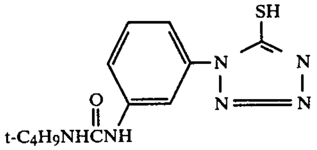
(II)-(11)
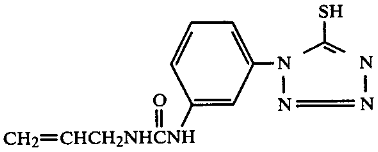
(II)-(12)
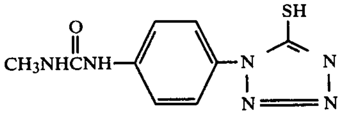
(II)-(13)
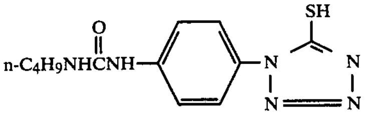
(II)-(14)
-continued
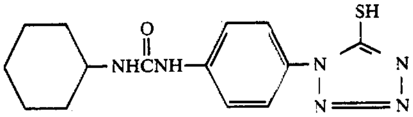
II)-(15)
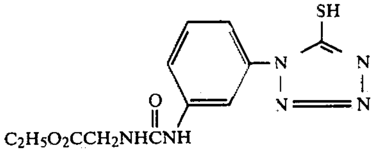
II)-(16)
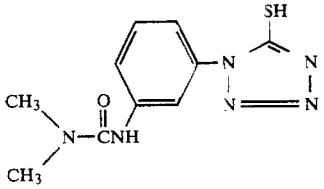
II)-(17)
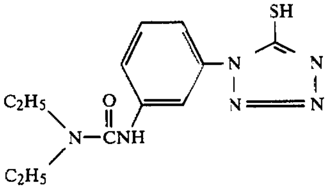
II)-(18)
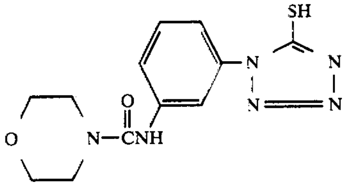
II)-(19)
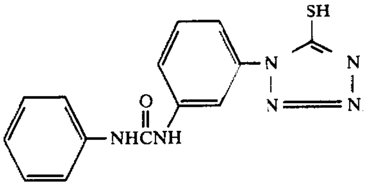
II)-(20)
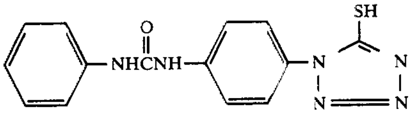
II)-(21)
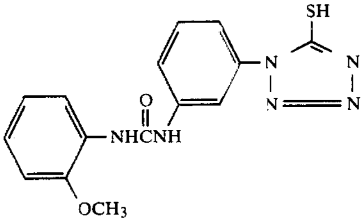
II)-(22)
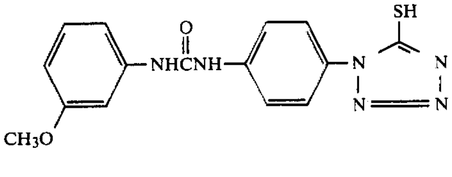
II)-(23)

-continued (II)-(24)

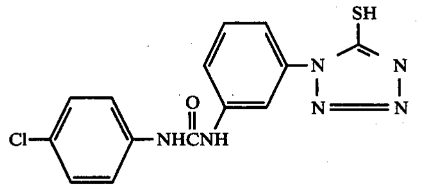

(II)-(25)

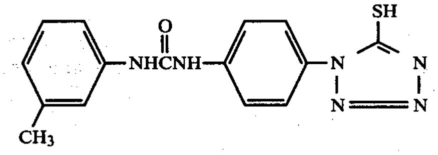

(II)-(26)

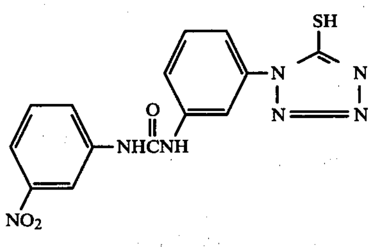

(II)-(27)

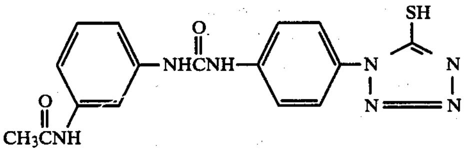

(II)-(28)

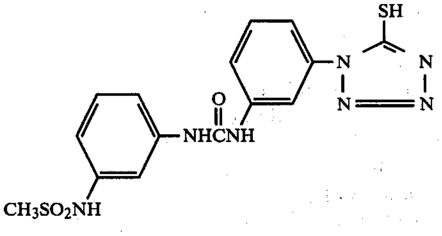

(II)-(29)

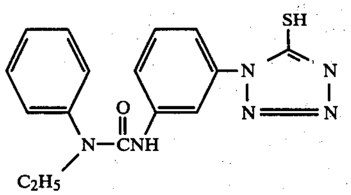

(II)-(30)

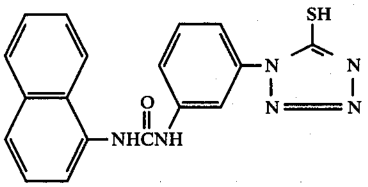

(II)-(31)

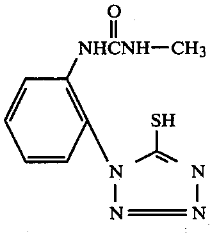

-continued (II)-(32)

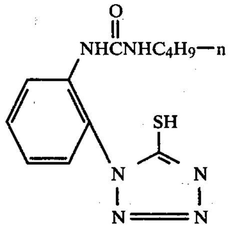

These compounds can be generally synthesized by reacting amino-substituted 1-phenyl-5-mercaptotetrazole, which is obtained by hydrolyzing the amido group of amido-substituted 1-phenyl-5-mercaptotetrazole described in Japanese Patent Applications (OPI) 37436/75 and 3231/76 and U.S. Pat. Nos. 3,295,976 and 3,376,310 with strong acid such as hydrochloric acid, with suitable isocyanic acid ester or N,N-di-substituted carbamoyl chloride. In the following, examples of processes for synthesizing them are described.

(1) Synthesis of Compound (II)-(5)

150 g (0.51M) of 1-(3-hexanamidophenyl)-5-mercaptotetrazole was dispersed in 450 ml of ethanol, and 300 ml of concentrated hydrochloric acid was added thereto with stirring at room temperature. After the reaction was carried out at room temperature for 3 hours, the mixture was cooled with ice, and the precipitated crystals were separated by filtration and washed with acetone to obtain 110 g of 1-(3-aminophenyl)-5-mercaptotetrazole hydrochloride. The resulting amine hydrochloride was dispersed in 750 ml of acetonitrile. After adding 485 ml of triethylamine, 125 g of butyl isocyanate was added dropwise at room temperature. After the reaction was carried out at room temperature for 6 hours, 2.2 liters of water were added and the pH was adjusted to 2 with hydrochloric acid. The precipitated crystals were separated by filtration and recrystallized from ethanol to obtain 69 g (yield: 46%) of the desired product having a melting point of 171°-172° C. (decomposition).

(2) Synthesis of Compound (II)-(18)

23 g of 1-(3-aminophenyl)-5-mercaptotetrazole and 32 g of pyridine were dispersed in 220 ml of acetonitrile, and 16 g of N,N-diethylcarbamoyl chloride was added dropwise thereto. After refluxing for 1.5 hours with heating, 200 ml of water was added and the solution was extracted with ethyl acetate. After being concentrated, the product was recrystallized from 250 ml of acetonitrile to obtain 15 g (yield: 51%) of the desired product having a melting point of 184°-185° C. (decomposition).

Other compounds can be synthesized by the same procedure as described above.

The amount of the compounds represented by the general formula (II) of the present invention to be used cannot be easily determined because it should be suitably varied according to the kind of the compound or the layer to which it is added. However, it has been found that variation of photographic properties during preservation and, particularly, occurrence of fogs are prevented if it is used in a range of $10^{-2}$ mol to $10^2$ mols based on 1 mol of silver. A more preferred amount is in a range of $10^{-1}$ mol to 10 mols based on 1 mol of silver.

The compound represented by the general formula (II) may be added to the layer to which the compound represented by the general formula (I) is added or they may be added to different layers, respectively. It is advantageous that the compound represented by the general formula (II) is added to layers containing colloidal silver (a yellow filter layer or an antihalation layer), because it is very effective for preventing the increase of fogs in the adjacent layer by the passage of time which is cuased by diffusion of colloidal silver into the adjacent layer to function as physical development nuclei.

In photographic emulsion layers of the color sensitive materials used in the present invention, the silver halide may be any of silver bromide, silver iodobromide, silver iodochlorobromide, silver chlorobromide or silver chloride. The average particle size of silver halide particles in the photographic emulsions (the particle size means the diameter in case of spherical or nearly spherical particles and the length of the side in case of cubic particles, and it is shown as an average based on projection areas) is not restricted, but $3\mu$ or less is preferred. The distribution of particle size may be broad or narrow.

The silver halide particles in the photographic emulsions may have a regular crystal form such as a cube or an octahedron, or may have an irregular crystal form such as a sphere or a plate, etc. They may have a composite crystal form of them. Further, the silver halide may be composed of a mixture of particles having various crystal forms.

The inner part and the surface layer of the silver halide particles may have different phases from each other, or the silver halide particles may be composed of a homogeneous phase. Further, they may be particles wherein the latent image is formed on, chiefly, the surface or may be particles wherein the latent image is formed in, chiefly, the inner part.

The photographic emulsions used in the present invention can be prepared by processes described in P. Glafkides, *Chimie et Physique Photographique* (issued by Paul Montel Co., 1967), G. F. Duffin, *Photographic Emulsion Chemistry* (issued by The Focal Press, 1966) and V. L. Zelikman et al., *Making and Coating Photographic Emulsion* (issued by The Focal Press, 1964), etc. Namely, they may be prepared by any process such as an acid process, a neutral process or an ammonia process. Further, various processes may be used as the process for reacting soluble silver salts with soluble halogen salts, such as any one-side mixing process, simultaneous mixing process or a combination of them.

A process for forming particles in a presence of excess silver ions (the so-called reverse mixing process) can be used. As one of simultaneous mixing processes, a process by which the pAg of the liquid phase for forming silver halide is kept constant, namely, the so-called controlled double jet process, can be used. According to this process, a silver halide emulsion having a regular crystal form and a nearly uniform particle size is obtained.

Two or more silver halide emulsions prepared separately may be used as a mixture.

Cadmium salts, zinc salts, lead salts, thallium salts, iridium salts or complex salts thereof, rhodium salts or complex salts thereof, or iron salts or complex salts thereof may be allowed to coexist when forming silver halide particles or carrying out physical ageing.

The present invention can be used for negative type emulsions which form surface latent images and direct reversal emulsions. Examples of the latter emulsions are internal latent image type emulsions and direct reversal emulsions previously fogged.

Examples of internal latent image type silver halide emulsions which can be advantageously used in the present invention include coacervation type emulsions described in U.S. Pat. Nos. 2,592,250, 3,206,313, 3,447,927, 3,761,276 and 3,935,014, etc., core/shell type emulsions and emulsions containing hetero metal, etc.

Examples of nucleus forming agents for these types of emulsions include hydrazines described in U.S. Pat. Nos. 2,588,982 and 2,563,785; hydrazides and hydrazones described in U.S. Pat. No. 3,227,552; quaternary salt compounds described in British Pat. No. 1,283,835, Japanese Patent Publication No. 38164/74 and U.S. Pat. Nos. 3,734,738, 3,719,494 and 3,615,615; sensitizing dyes which have a substituent having a nucleating function in the dye molecule, described in U.S. Pat. No. 3,718,470; and acylhydrazinophenylthiourea compounds described in U.S. Pat. Nos. 4,030,925 and 4,031,127.

Although the silver halide emulsions can be used without carrying out chemical sensitization, in a state of the so-called primitive emulsion, they are generally chemically sensitized. In order to carry out chemical sensitization, it is possible to use processes described in the above-mentioned books written by Glafkides and Zelikman and *Die Grundlagen der Photographischen Prozesse mit Silberhalogeniden*, edited by H. Frieser (Akademische Verlagsgesellschaft, 1968).

Namely, a sulfur sensitization process using sulfur containing compounds or activated gelatin capable of reacting with silver ions, a reduction sensitization process using reducing substances and a noble metal sensitization process using gold or other noble metal compounds, etc., can be used alone or as a combination thereof. Examples of useful sulfur sensitizers include thiosulfates, thioureas, thiazoles, rhodanines and other compounds, examples of which have been described in U.S. Pat. Nos. 1,574,944, 2,410,689, 2,278,947, 2,728,668 and 3,656,955. Examples of useful reducing sensitizers include stannous salts, amines, hydrazine derivatives, formamidine sulfinic acid and silane compounds, etc., examples of which have been described in U.S. Pat. Nos. 2,487,850, 2,419,974, 2,518,698, 2,983,609, 2,983,610 and 2,694,637. In order to carry out noble metal sensitization, it is possible to use complex salts of metal of group VIII in the Periodic Table, such as platinum, iridium or palladium, etc., as well as gold complex salts, examples of which have been described in U.S. Pat. Nos. 2,399,083 and 2,448,060 and British Patent No. 618,061, etc.

The photographic emulsions may be spectrally sensitized with methine dyes or others. Examples of dyes used include cyanine dyes, merocyanine dyes, composite cyanine dyes, composite merocyanine dyes, holopolar cyanine dyes, hemicyanine dyes, styryl dyes and hemioxonol dyes. Particularly useful dyes are those belonging to cyanine dyes, merocyanine dyes and composite merocyanine dyes.

Useful sensitizing dyes include those described in, for example, German Pat. No. 929,080, U.S. Pat. Nos. 2,231,658, 2,493,748, 2,503,776, 2,519,001, 2,912,329, 3,655,394, 3,656,959, 3,672,897 and 3,694,217, British Pat. No. 1,242,588 and Japanese Patent Publication No. 14030/69.

In addition to the above described silver halide emulsion layers having sensitivity, a substantially insensitive microgranular silver halide emulsion layer may be provided in order to improve granularity or sharpness or for other purposes. Such a substantially insensitive microgranular emulsion layer can be provided on a sensitive silver halide emulsion layer or between a sensitive silver halide emulsion layer and a colloidal silver layer (a yellow filter layer or an antihalation layer).

The sensitive materials of the present invention may contain polyalkylene oxide or derivatives thereof such as ethers, esters or amides, etc., thioether compounds, thiomorpholines, quaternary ammonium compounds, urethane derivatives, urea derivatives, imidazole derivatives and 3-pyrazolidones, etc., for the purpose of increasing sensitivity, improving contrast or accelerating development. For example, substances described in U.S. Pat. Nos. 2,400,532, 2,423,549, 2,716,062, 3,617,280, 3,772,021 and 3,808,003, etc., can be used.

Examples of binders used in photographic emulsion layers and other layers include gelatin which is advantageously used, but other hydrophilic colloids may be used. Examples of them include proteins such as gelatin derivatives, graft polymers of gelatin with other high polymer, albumin or casein, etc.; saccharose derivatives such as cellulose derivatives such as hydroxyethyl cellulose, carboxymethyl cellulose or cellulose sulfate, etc., sodium alginate or starch derivatives, etc.; and hydrophilic synthetic high molecular substances such as homo- or copolymers such as polyvinyl alcohol, polyvinyl alcohol partial acetal, poly-N-vinylpyrrolidone, polyacrylic acid, polymethacrylic acid, polyacrylamide, polyvinyl imidazole or polyvinyl pyrazole, etc.

Examples of useful gelatins include not only lime-treated gelatin but also acid-treated gelatin and enzyme-treated gelatin described in *Bull. Soc. Sci. Phot. Japan,* No. 16, page 30 (1966). Further, hydrolyzed products and enzymatic decomposition products of gelatin can be used. Useful gelatin derivatives include those prepared by reacting gelatin with various compounds, for example, acid halides, acid anhydrides, isocyanates, bromoacetic acid, alkanesultones, vinyl sulfonamides, maleinimide compounds, polyalkylene oxides and epoxy compounds. Examples of them have been described in U.S. Pat. Nos. 2,614,928, 3,132,945, 3,186,846 and 3,312,553, British Pat. Nos. 861,414, 1,033,189 and 1,005,784 and Japanese Patent Publication No. 26845/67, etc.

The above-described gelatin graft polymers may be a substance prepared by grafting gelatin with a homo- or copolymer of vinyl type monomers such as acrylic acid, methacrylic acid or derivatives of them, such as esters or amides, etc., acrylonitrile or styrene, etc. It is particularly preferred to use graft polymers of gelatin with polymers having a certain degree of compatibility with gelatin, for example, polymers of acrylic acid, methacrylic acid, acrylamide, methacrylamide or hydroxyalkyl methacrylate, etc. Examples of them have been described in U.S. Pat. Nos. 2,763,625, 2,831,767 and 2,956,884, etc.

Examples of typical hydrophilic synthetic high molecular substances include those described in German Patent Application (OLS) No. 2,312,708, U.S. Pat. Nos. 3,620,751 and 3,879,205 and Japanese Patent Publication No. 7561/68.

The sensitive materials of the present invention may contain various compounds as an antifogging agent or a stabilizing agent together with the compounds represented by the general formula (II). Namely, it is possible to add many compounds known as antifogging agents or stabilizing agents, such as azoles, for example, benzothiazolium salts, nitroimidazoles, triazoles, benzotriazoles and benzimidazoles (particularly, nitro- or halogen substituted substances); heterocyclic mercapto compounds, for example, mercaptothiazoles, mercaptobenzothiazoles, mercaptobenzimidazoles, mercaptothiadiazoles, mercaptotetrazoles (particularly, 1-phenyl-5-mercaptotetrazole), and mercaptopyrimidines; the above-described heterocyclic mercapto compounds having water soluble groups such as a carboxyl group or a sulfonic acid group, etc.; thioketo compounds, for example, oxazolinethione; azaindenes, for example, tetraazaindenes (particularly, 4-hydroxy substituted-(1,3,3a,7)tetraazaindenes); benzenethiosulfonic acids; or benzenesulfinic acids, etc.

Detailed examples of them and methods of using them are disclosed in, for example, U.S. Pat. Nos. 3,954,474, 3,982,947 and 4,021,248 and Japanese Patent Publication No. 28660/77.

In the photographic sensitive materials of the present invention, the photographic emulsion layers and other layers may contain inorganic or organic hardening agents. Examples of these agents include chromium salts (chromium alum and chromium acetate, etc.), aldehydes (formaldehyde, glyoxal and glutaraldehyde, etc.), N-methylol compounds (dimethylolurea and methylol dimethylhydantoin, etc.), dioxane derivatives (2,3-dihydroxydioxane, etc.), active vinyl compounds (1,3,5-triacryloylhexahydro-s-triazine and 1,3-vinylsulfonyl-2-propanol, etc.), active halogen compounds (2,4-dichloro-6-hydroxy-s-triazine, etc.), or mucohalogenic acids (mucochloric acid and mucophenoxychloric acid, etc.), etc., which can be used alone or as a combination thereof.

The photographic emulsion layers and other layers in the sensitive materials of the present invention may contain various surface active agents for various purposes, for example, coating assistants, prevention of static charges, improvement of slipping property, emulsification and dispersion, prevention of adhesion and improvement of photographic properties (for example, acceleration of development, hardening of tone, and sensitization), etc.

For example, it is possible to use nonionic surface active agents such as saponin (steroid type), alkylene oxide derivatives (for example, polyethylene glycol, polyethylene glycol/polypropylene glycol condensation product, polyethylene glycol alkyl ethers, polyethylene glycol alkylaryl ethers, polyethylene glycol esters, polyethylene glycol sorbitan esters, polyalkylene glycol alkylamines or amides, and polyethylene oxide addition products of silicone, etc.), glycidol derivatives (for example, alkenylsuccinic acid polyglyceride and alkylphenol polyglyceride), aliphatic acid esters of polyhydric alcohols or alkyl esters of saccharoses, etc.; anionic surface active agents having acid groups such as a carboxyl group, sulfonic acid group, phosphonic acid group, sulfuric acid ester group or phosphoric acid ester group, etc., such as alkylcarboxylic acid salts, alkyl sulfonic acid salts, alkylbenzenesulfonic acid salts, alkylnaphthalenesulfonic acid salts, alkylsulfuric acid esters, alkylphosphoric acid esters, N-acyl-N-alkyltaurines, sulfosuccinic acid esters, sulfoalkyl polyoxyethylene alkylphenyl ethers or polyoxyethylene alkylphosphoric acid esters, etc.; amphoteric surface active agents such as amino acids, aminoalkylsulfonic acids, aminoalkylsulfuric or phosphoric acid esters, alkylbetaines or amineoxides, etc.; and cationic surface active agents such as alkylamine salts, aliphatic or aromatic quaternary ammonium salts, heterocyclic ammonium salts such as pyridinium or imidazolium salts, etc., and aliphatic or heterocyclic phosphonium or sulfonium salts, etc.

The photographic emulsion layers in the sensitive materials of the present invention may contain color forming couplers, namely, compounds capable of coloring by oxidative coupling with aromatic primary amine developing agents (for example, phenylenediamine derivatives and aminophenol derivatives, etc.) in the color development processing. Examples of magenta couplers include 5-pyrazolone couplers, pyrazolobenzimidazole couplers, cyanoacetylcoumarone couplers and opened chain acylacetonitrile couplers, etc. Examples of yellow couplers include acylacetamide couplers (for example, benzoylacetanilides, and pivaloylacetanilides), etc. Examples of cyan couplers include naphthol couplers and phenol couplers. It is preferred that these couplers are indiffusible couplers having a hydrophobic group called a ballast group in the molecule. The couplers may be any of 4-equivalent type and 2-equivalent type with respect to silver ions. Further, colored coupler having an effect of color correction or couplers which release a development inhibitor by development (the so-called DIR coupler) may be used. Further, non-coloring DIR coupling compounds which form a colorless product by a coupling reaction and release a development inhibitor, or DIR redox compounds may be used.

Examples of magenta forming couplers include those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German Patent Applications (OLS) Nos. 2,408,665, 2,417,945, 2,418,959 and 2,424,467, Japanese Patent Publication No. 6031/65, and Japanese Patent Applications (OPI) Nos. 20826/76, 13041/75, 58922/77, 129538/74, 74027/74, 159336/75, 42121/77, 74028/74, 60233/75, 26541/76 and 55122/78, etc.

Examples of yellow forming couplers include those described in U.S. Pat. Nos. 2,875,057, 3,265,506, 3,408,194, 3,551,155, 3,582,322, 3,725,072 and 3,891,445, German Patent No. 1,547,868, German Patent Applications (OLS) Nos. 2,219,917, 2,261,361 and 2,414,006, British Pat. No. 1,425,020, Japanese Patent Publication No. 10783/76, and Japanese Patent Applications (OPI) Nos. 26133/72, 73147/73, 102636/76, 6341/75, 123342/75, 130442/75, 21827/76, 87650/75, 82424/77 and 115219/77, etc.

Examples of cyan forming couplers include those described in U.S. Pat. Nos. 2,369,929, 2,434,272, 2,472,293, 2,521,908, 2,895,826, 3,034,892, 3,311,476, 3,458,315, 3,476,563, 3,583,971, 3,591,383, 3,767,411 and 4,004,929, German Patent Applications (OLS) Nos. 2,414,830 and 2,454,329, and Japanese Patent Applications (OPI) Nos. 59838/73, 26034/76, 5055/73, 146828/76, 69624/77 and 90932/77.

Examples of colored couplers include those described in, for example, U.S. Pat. Nos. 3,476,560, 2,521,908 and 3,034,892, Japanese Patent Publications Nos. 2016/69, 22335/63, 11304/67 and 32461/69, Japanese Patent Applications (OPI) Nos. 26034/76 and 42121/77 and German Patent Application (OLS) No. 2,418,959.

Examples of DIR couplers include o-aminoazo type DIR couplers described in U.S. Pat. No. 3,148,062, thioether type DIR couplers described in U.S. Pat. No. 3,227,554, 2-benzotriazolyl type DIR couplers described in U.S. Pat. No. 3,617,291, 1-benzotriazolyl type DIR couplers described in German Patent Application (OLS) No. 2,414,006 and Japanese Patent Applications (OPI) Nos. 82424/77 and 117627/77, nitrogen-containing heterocyclic substituted acetic acid ester type DIR couplers described in Japanese Patent Applications (OPI) Nos. 30591/75 and 82423/77, 2-equivalent type DIR cyan couplers described in Japanese Patent Applications (OPI) Nos. 90932/77 and 146828/76, and malondiamide type DIR couplers described in Japanese Patent Application (OPI) No. 69624/77, etc.

Examples of non-coloring DIR coupling compounds include thioether type cyclic non-coloring DIR compounds described in British Pat. No. 1,423,588, German Patent Applications (OLS) Nos. 2,405,442, 2,523,705, 2,529,350 and 2,448,063 and U.S. Pat. No. 3,938,996, thioether type chain non-coloring DIR compounds described in U.S. Pat. Nos. 3,632,345 and 3,928,041, benzotriazole type non-coloring DIR compounds described in Japanese Patent Applications (OPI) Nos. 147716/75, 105819/76 and 67628/77, and picolinium type DIR coupling compounds described in Japanese Patent Application (OPI) No. 72433/76, etc.

Examples of DIR redox compounds include DIR hydroquinones described in U.S. Pat. No. 3,639,417, German Patent Application (OLS) No. 2,460,202 and U.S. Pat. No. 3,297,445, and DIR redox type couplers described in Japanese Patent Application (OPI) No. 57828/77, etc.

The sensitive materials of the present invention are capable of containing developing agents. Examples of the developing agents include those described in *Research Disclosure,* Vol. 176, page 29, in the column of "Developing agents".

The photographic emulsion layers and other layers in the sensitive materials of the present invention may contain dyes as filter dyes or for the purpose of preventing irradiation, etc. Examples of such dyes include those described in *Research Disclosure,* Vol. 176, pages 25–26, in the column of "Absorbing and filter dyes".

The sensitive materials of the present invention may contain antistatic agents, plasticizers, matting agents, lubricants, ultraviolet ray absorbing agents, fluorescent whitening agents, and anti-air-fogging agents.

The silver halide emulsion layers and/or the other layers are coated on a base. Methods of coating are described in *Research Disclosure,* Vol. 176, pages 27–28, in the column of "Coating procedures".

When color sensitive materials having the above-described characteristics are used as color negative films, color positive films or color papers, they are generally subjected to processings comprising (1) color development→stopping→water washing→bleach accelerating bath→bleaching with persulfate→water washing→fixing→water washing→stabilization→drying, after being exposed imagewise to light. In the process (1), a previous bath and a hardening bath may be provided before the color development, and the water washing after the stopping, bleach accelerating bath and bleaching with persulfate can be omitted. Further, the bleach accelerating bath may be omitted.

On the other hand, when they are used as color reversal films, they are generally subjected to processings comprising (2) black and white development→stopping→water washing→fogging→water washing→color development→stopping→water washing→bleach accelerating bath→water washing→bleaching with persulfate→water washing→fixing→water washing→stabilization→drying. In the process (2), a previous bath, a prehardening bath or a neutralizing bath, etc., may be provided. Further, the water washing after the stopping, fogging, bleach accelerating bath or bleaching may be omitted. The fogging bath can be replaced with re-exposure to light or can be omitted by adding the fogging agent to the color developing bath. Further, the bleach accelerating bath can be omitted.

The color developing solution generally consists of an aqueous alkaline solution containing a color developing agent. Examples of useful color developing agent include known primary aromatic amine developing agents such as phenylenediamines (for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline and 4-amino-3-methyl-N-ethyl-N-β-methoxyethylaniline, etc.).

In addition, substances described in L. F. A. Mason, *Photographic Processing Chemistry,* pages 226–229 (Focal Press, 1966), U.S. Pat. Nos. 2,193,015 and 2,592,364 and Japanese Patent Application (OPI) No. 64933/73 may be used.

The color developing solution can contain pH buffer agents such as sulfites, carbonates, borates and phosphates of alkali metals, and development inhibitors or antifogging agents such as bromides, iodides, or organic antifoggants, etc. If desired, the color developing solution may contain water softeners, preservatives such as hydroxylamine, organic solvents such as benzyl alcohol or diethylene glycol, development accelerators such as polyethylene glycol, quaternary ammonium salts or amines, dye forming couplers, competitive couplers, fogging agents, such as sodium borohydride, auxiliary developing agents such as 1-phenyl-3-pyrazolidone, viscosity imparting agents, polycarboxylic acid chelating agents described in U.S. Pat. No. 4,083,723, and antioxidants described in German Patent Application (OLS) No. 2,622,950, etc.

The emulsion layers, after carrying out color development, are bleached with persulfates. The bleaching and fixation may be carried out at the same time or may be carried out respectively.

Persulfates used as a bleaching agent in the present invention are alkali metal persulfates such as potassium persulfate or sodium persulfate, and ammonium persulfate.

A preferred amount of the above described bleaching agent is in a range from 0.05 to 2 mols per liter of the bleaching solution.

Examples of the persulfate bleaching solution include those described in James, *The Theory of the Photographic Process,* pp. 449–450 (Macmillan Publishing Co., Inc., 1977) and *Research Disclosure,* No. 15704 (May, 1977).

Typical persulfate bleaching solution has the following composition.

| | |
|---|---|
| Sodium persulfate | 60 g |
| Sodium chloride | 20 g |
| Sodium dihydrogen phosphate | 15 g |
| Sodium tetrapolyphosphate | 2 g |
| β-Alanine | 2 g |
| Phosphoric acid (85%) | 2 g |
| Water to make | 1 liter |

The bleaching solution may contain chlorides such as potassium chloride, sodium chloride or ammonium chloride, or bromides such as potassium bromide, sodium bromide or ammonium bromide, etc. However, in practical application bromides are difficult to use because they produce a bromine gas. A preferred amount of the above described halides is in a range from 0.1 to 2 mols per liter of the bleaching solution. Further, to the bleaching solution, it is possible to add one or more of inorganic acids, organic acids and salts thereof having a pH buffer function, such as boric acid, borax, sodium metaborate, acetic acid, sodium acetate, sodium carbonate, potassium carbonate, phosphorous acid, phosphoric acid, sodium phosphate, citric acid, sodium citrate and tartaric acid, etc. Further, it is possible to control the salt concentration in the bleaching solution by adding salts such as sodium sulfate or potassium sulfate, etc.

Further, imide compounds described in Japanese Patent Application (OPI) No. 149944/80 for preventing generation of halogen gas may be added to the bleaching solution in an amount of ranging from $2\times10^{-6}$ to $1\times10^{-1}$ mol and, preferably, $1\times10^{-2}$ to $4\times10^{-2}$ mol per liter of the bleaching solution.

It is preferred that the pH of the bleaching solution used be 1.0 to 7.0 and, preferably, 1.5 to 3.5.

In the bleaching solution used in the present invention or the previous bath thereof, various bleach accelerating agents can be used, though they are not always required. For example, it is possible to use bleach accelerating agents such as mercapto compounds or dithiocarbamate compounds, described in U.S. Pat. Nos. 3,707,374, 3,772,020 and 3,893,858, Japanese Patent Publication No. 28227/76, Japanese Patent Applications (OPI) Nos. 94927/78, 95631/78, 97980/78 and 98901/78, and *Research Disclosure,* No. 15704 (May, 1977).

Conventional fixing solutions can be used. Useful fixing agents include not only thiosulfates and thiocyanates but also organic sulfur compounds whose effect as a fixing agent is known. The fixing solution may contain water-soluble aluminum salts as hardeners.

In the following, the present invention is illustrated in greater detail with reference to examples.

EXAMPLE 1

A multilayer color sensitive material composed of layers having the following compositions provided on a cellulose triacetate film base was produced.

Layer-1 Antihalation layer:

40 cc of a 5 weight % aqueous solution of the coating agent: sodium p-dodecylbenzenesulfonate was added to 1 kg of a black colloidal silver emulsion (containing 15 g of blacked silver and 100 g of gelatin in 1 kg of the emulsion), and the emulsion was applied so as to result in a dry film thickness of 2μ.

Layer-2 Gelatin intermediate layer (dry film thickness: 1.0μ)

Layer-3 Red-Sensitive low-speed silver halide emulsion layer:

A silver iodobromide emulsion containing 5 mol% of iodine (average particle size: 0.3μ, containing 100 g of silver halide and 70 g of gelatin in 1 kg of the emulsion) was prepared by a conventional method. To 1 kg of this emulsion, 210 cc of a 0.1% solution of anhydro-5,5-dichloro-9-ethyl-B 3,3′-di(3-sulfopropyl)thiacarbocyanine hydroxide pyridinium salt in methanol was added as a red-sensitive spectral sensitizer, and then 20 cc of a 5 weight % aqueous solution of 5-methyl-7-hydroxy-2,3,4-triazaindolizine and 400 g of the cyan coupler emulsion (1) and 200 g of the emulsion (2) having the following compositions were added. Thereafter, 200 cc of a 2% aqueous solution of colored cyan coupler (CC-1) was added and 30 cc of a 2 weight % aqueous solution of 2-hydroxy-4,6-dichlorotriazine sodium salt as a gelatin hardener was added thereto to prepare a red-sensitive low-speed silver halide emulsion. This emulsion was applied so as to result in a dry film thickness of 3.5μ.

CC-1

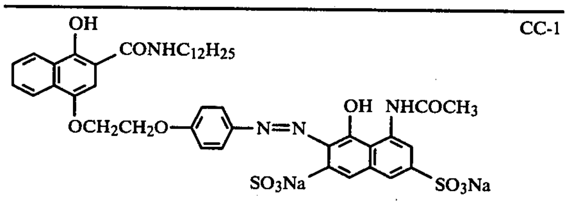

Emulsion (1)

| | | | |
|---|---|---|---|
| (1) | 10 weight % aqueous solution of gelatin | 1,000 | g |
| (2) | Sodium p-dodecylbenzenesulfonate | 5 | g |
| | Tricresyl phosphate | 60 | cc |
| | Cyan coupler (C-101) | 70 | g |
| | Ethyl acetate | 100 | cc |

After the mixture (2) was dissolved at 55° C., it was added to (1) previously heated to 55° C., and the resulting mixture was emulsified by a colloid mill.

C-101

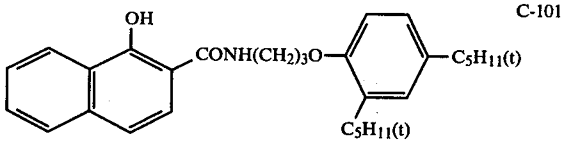

Emulsion (2)

| | | | |
|---|---|---|---|
| (1) | 10 weight % aqueous solution of gelatin | 1,000 | g |
| (2) | Sodium p-dodecylbenzenesulfonate | 5 | g |
| | Tricresyl phosphate | 60 | cc |
| | Cyan coupler (C-101) | 70 | g |
| | DIR Compound (D-1) | 10 | g |
| | Ethyl acetate | 100 | cc |

After the mixture (2) was dissolved at 55° C., it was added to (1) previously heated to 55° C., and the resulting mixture was emulsified by a colloid mill.

D-1

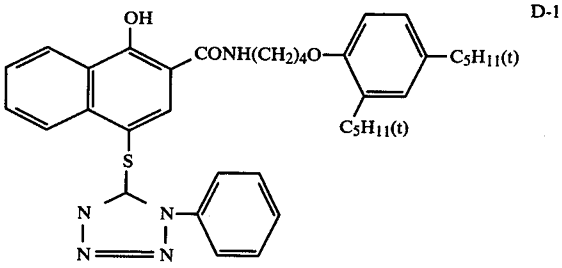

Layer-4 Red-sensitive high-speed silver halide emulsion:

In the silver halide emulsion of Layer-3, the following modification was carried out.

| | |
|---|---|
| Average particle size of the silver iodobromide emulsion | 0.9μ |

-continued

| | |
|---|---|
| Amount of the red-sensitive spectral sensitizer added | 140 cc |
| Emulsion (1) | 220 g |
| Emulsion (2) | 30 g |

The resulting silver halide emulsion was applied so as to result in a dry film thickness of 2.2μ.

Layer-5 Gelatin intermediate layer (dry film thickness: 0.8μ)

Layer-6 Greeen-sensitive low-speed silver halide emulsion:

To 1 kg of a silver iodobromide emulsion used in the Layer-3, 180 cc of a 0.1% solution of 3,3'-di-(2-sulfoethyl)-9-ethylbenzoxacarbocyanine pyridinium salt in methanol, as a green-sensitive spectral sensitizer, and 20 cc of a 5 weight % aqueous solution of 5-methyl-7-hydroxy-2,3,4-triazaindolizine were added in order, and thereafter 320 g of the magenta coupler emulsion (3) and 180 g of the emulsion (4) having the following compositions were added thereto. Further, 50 cc of a 2 weight % aqueous solution of 2-hydroxy-4,6-dichlorotriazine sodium salt was added as a gelatin hardener to produce a green-sensitive low-speed silver halide emulsion. This emulsion was applied so as to result in a dry film thickness of 3.2μ.

Emulsion (3)

| | | | |
|---|---|---|---|
| (1) | 10 weight % aqueous solution of gelatin | 1,000 | g |
| (2) | Sodium p-dodecylbenzenesulfonate | 5 | g |
| | Tricresyl phosphate | 80 | cc |
| | Magenta coupler (M-101) | 50 | g |
| | Colored magenta coupler (CM-1) | 10 | g |
| | Ethyl acetate | 120 | cc |

After the mixture (2) was dissolved at 55° C., it was added to (1) previously heated to 55° C., and the resulting mixture was emulsified by a colloid mill.

M-101

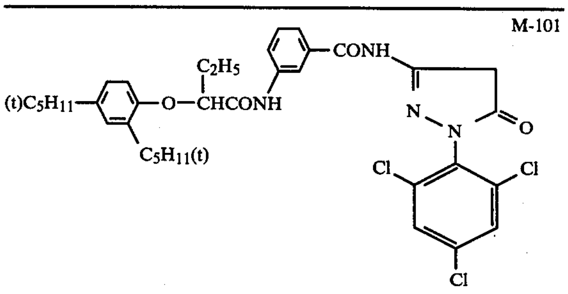

CM-1

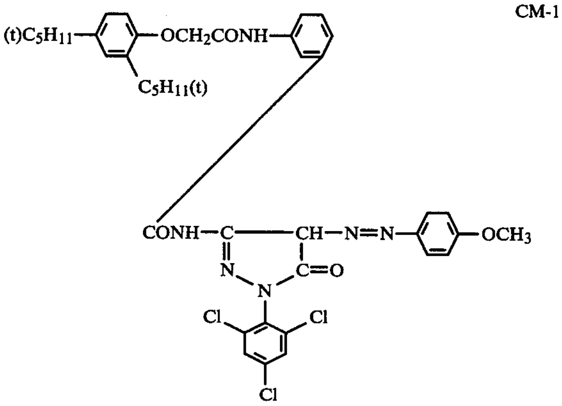

Emulsion (4)

| | | | |
|---|---|---|---|
| (1) | 10 weight % aqueous solution of gelatin | 1,000 | g |
| (2) | Sodium p-dodecylbenzenesulfonate | 5 | g |
| | Tricresyl phosphate | 80 | cc |
| | Magenta coupler (M-101) | 50 | g |
| | Colored magenta coupler (CM-1) | 10 | g |
| | DIR Compound (D-2) | 15 | g |
| | Ethyl acetate | 120 | cc |

After the mixture (2) was dissolved at 55° C., it was added to (1) previously heated to 55° C., and the resulting mixture was emulsified by a colloid mill.

D-2

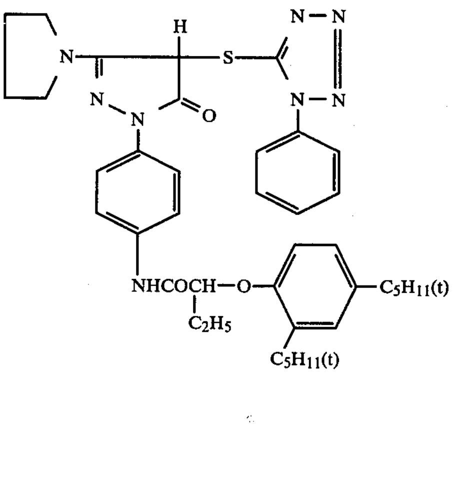

Layer-7 Green-sensitive high-speed silver halide emulsion layer:

In the silver halide emulsion layer of Layer-6, the following modification was carried out.

| | |
|---|---|
| Average particle size of the silver iodobromide emulsion | 1.0μ |
| Iodine content of the emulsion | 6.5 mol % |
| Amount of the green-sensitive spectral sensitizer added | 100 cc |
| Emulsion (3) | 150 g |
| Emulsion (4) | 30 g |

The resulting silver halide emulsion was applied so as to result in a dry film thickness of 2.2μ.

Layer-8 Yellow colloidal silver layer (dry film thickness: 1.6μ)

Layer-9 Blue-sensitive low-speed silver halide emulsion layer:

To 1 kg of the same silver iodobromide emulsion as that used in the Layer-3 except that the average particle size was 0.5μ, 20 cc of a 5 weight % aqueous solution of 5-methyl-7-hydroxy-2,3,4-triazaindolizine and 1,500 g of the yellow coupler emulsion (5) having the following composition were added. Further, 50 cc of a 2 weight % aqueous solution of 2-hydroxy-4,6-dichlorotriazine sodium salt was added as a gelatin hardener to prepare a blue-sensitive low-speed silver halide emulsion.

The resulting emulsion was applied so as to result in a dry film thickness of 3.0μ.

| | Emulsion (5) | | |
|---|---|---|---|
| (1) | 10 weight % aqueous solution of gelatin | 1,000 | g |
| (2) | Sodium p-dodecylbenzenesulfonate | 5 | g |
| | Tricresyl phosphate | 80 | cc |
| | Yellow coupler (Y-1) | 100 | g |
| | Ethyl acetate | 120 | cc |

After the mixture (2) was dissolved at 55° C., it was added to (1) previously heated to 55° C., and the resulting mixture was emulsified by a colloid mill.

Y-1

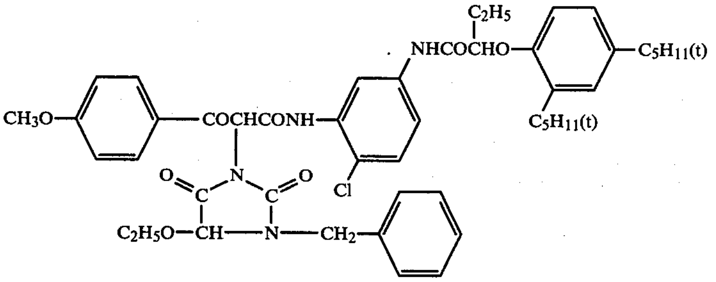

Layer-10 Blue-sensitive high-speed silver halide emulsion layer:

In the silver halide emulsion of the Layer-9, the following modification was carried out.

| | |
|---|---|
| Average particle size of the silver | 1.1μ |

-continued

| | |
|---|---|
| iodobromide emulsion | |
| Emulsion (5) | 300 g |

The resulting silver halide emulsion was applied so as to result in a dry film thickness of 2.5μ.

Layer-11 Gelatin protective layer (dry film thickness: 1.5μ)

The sample prepared as described above was named Film (A).

A 0.1 weight % aqueous solution of Compound (I)-(1) was added to the antihalation layer in Film (A) in amounts as shown in Table 1 to produce Films (B) to (E).

To the yellow filter layer in Film (A), 2.1 mols per mol of colloidal silver, of Compound (II)-(2) and 1-phenyl-5-mercaptotetrazole (solution in methanol) were added, respectively, to produce Films (F) and (G).

Using Films (A) to (G) produced as described above, a compulsory time passage test was carried out as follows.

| Conditions of Compulsory Time Passage Test: | | |
|---|---|---|
| (1) | Preservation at room temperature | 3 Days (fresh) |
| (2) | Preservation at 50° C., 60% RH | 3 Days (dry) |
| (3) | Preservation at 45° C., 80% RH | 3 Days (wet) |

Then, wedge exposure was carried out and thereafter the following development processing was carried out. By self-recording densitometry, a characteristic curve of the green-sensitive layer adjacent to the yellow filter layer was determined, from which the lowest density $D_{min}$ and the relative logarithmic density $S_{0.2}$ (measured at an exposure of giving a density of fog +0.2) of the green-sensitive layer were determined. Changes of each resulting value under preservation conditions are shown in Table 1.

| Processing Step | Temperature | Time |
|---|---|---|
| Color Development | 41° C. | 3 minutes |
| Stopping | 38° C. | 30 seconds |
| Water Washing | " | 30 seconds |
| Bleach Accelerating | " | 30 seconds |
| Bleaching | " | 1 minute or 3 minutes |
| Water Washing | " | 1 minute |
| Fixation | " | 2 minutes |
| Water Washing | " | 2 minutes |
| Stabilizing Bath | " | 10 seconds |

Treating solutions used had the following compositions.

| | |
|---|---|
| Color Developing Solution | |
| Sodium Hydroxide | 2 g |
| Sodium Sulfite | 2 g |
| Potassium Bromide | 1.4 g |
| Sodium Chloride | 1 g |
| Borax | 1 g |
| Hydroxylamine Sulfate | 4 g |
| Disodium Ethylenediaminetetraacetate | 2 g |
| 4-Amino-3-methyl-N—ethyl-N—(β-hydroxy-ethyl)aniline Monosulfate | 4 g |
| Water to make | 1 liter |
| Stopping Solution | |
| Water | 800 ml |
| Glacial Acetic Acid | 30 ml |
| Caustic Soda | 1.65 g |
| Water to make | 1 liter |
| Bleach Accelerating Bath | |
| Sodium Sulfite (anhydrous) | 9.0 g |
| 2-N,N—Dimethylaminoethylisothiourea Dihydrochloride | 2.5 g |
| Sodium Acetate | 8.0 g |
| Glacial Acetic Acid | 2.3 ml |
| Water to make | 1 liter |
| Bleaching Solution | |
| Sodium Persulfate | 60 g |
| Sodium Chloride | 20 g |
| Sodium Dihydrogen Phosphate | 15 g |
| Sodium Tetrapolyphosphate | 2 g |
| β-Alanine | 2 g |
| Phosphoric Acid (85%) | 2.2 ml |
| Water to make | 1 liter |
| Fixing Solution | |
| Sodium Thiosulfate | 150 g |
| Sodium Sulfite (anhydrous) | 15 g |
| Borax | 12 g |
| Glacial Acetic Acid | 15 ml |
| Water to make | 1 liter |
| Stabilizing Bath | |
| Formaldehyde (37%) | 10 ml |
| Water to make | 1 liter |

TABLE 1

| Film No. | Compound (I)-(1) ($mg/m^2$) | Compound (II)-(2) (mol/mol of colloidal silver) | Total Silver Content ($g/m^2$) | $D_{min}$ of Green-Sensitive Layer Fresh | Dry | Wet | $S_{0.2}$ of Green-Sensitive Layer Fresh | Dry | Wet | Residual Silver Content after Processing: Bleaching for 1 Min ($\mu g/cm^2$) | Bleaching for 3 Min ($\mu g/cm^2$) |
|---|---|---|---|---|---|---|---|---|---|---|---|
| A | 0 | 0 | 7.5 | 0.60 | 0.59 | 0.68 | −2.23 | −2.26 | −2.05 | 17 | 2.5 |
| B | 0.35 | 0 | " | 0.60 | 0.59 | 0.68 | −2.23 | −2.26 | −2.05 | 12 | 2.0 |
| C | 0.70 | 0 | " | 0.60 | 0.59 | 0.68 | −2.23 | −2.26 | −2.05 | 5.0 | 1.8 |
| D | 1.40 | 0 | " | 0.60 | 0.59 | 0.68 | −2.23 | −2.26 | −2.05 | 4.6 | 1.8 |
| E | 2.80 | 0 | " | 0.60 | 0.59 | 0.68 | −2.23 | −2.26 | −2.05 | 2.0 | 1.5 |
| F | 2.80 | 2.1 | " | 0.55 | 0.54 | 0.57 | −2.21 | −2.20 | −2.08 | 1.8 | 1.3 |
| G | 2.80 | 2.1 (comparative compound*) | " | 0.55 | 0.54 | 0.63 | −2.20 | −2.22 | −2.03 | 2.5 | 1.7 |

*Comparative compound: 1-Phenyl-5-mercaptotetrazole

It is obvious from Table 1, when the compound represented by the general formula (I) of the present invention is added to the antihalation layer, the desilvering rate remarkably increases and, consequently, the bleaching time can be shortened.

Further, when the compound represented by the general formula (II) of the present invention is used together, not only the increase of fogs and the deterioration of sensitivity in the adjacent layer which are caused by the presence of colloidal silver can be prevented, but also the desilvering rate is not reduced but has somewhat of a tendency to increase even though the compound represented by the general formula (II) is present.

On the contrary, the prior known antifogging agent: 1-phenyl-5-mercaptotetrazole is not effective in preventing the increase of fogs and reduction of sensitivity in the adjacent layer.

EXAMPLE 2

Using the Films (A) to (E) in Example 1, step-wedge exposure was carried out and, subsequently, development was carried out as follows. The residual silver content of the lowest density step was measured. The residual silver contents are shown in Table 2.

| Processing Step | Temperature | Time |
|---|---|---|
| Color Development | 41° C. | 3 minutes |
| Stopping | 38° C. | 30 seconds |
| Water Washing | " | 30 seconds |
| Bleaching | " | 3 minutes or 6 minutes |
| Water Washing | " | 1 minute |
| Fixation | " | 2 minutes |
| Water Washing | " | 2 minutes |
| Stabilizing Bath | " | 10 seconds |

Treating solutions used are the same as those in Example 1.

TABLE 2

| Film No. | Compound (I)-(1) ($mg/m^2$) | Total Silver Content ($g/m^2$) | Residual Silver Content after Processing: Bleaching for 3 Min ($\mu g/cm^2$) | Residual Silver Content after Processing: Bleaching for 6 Min ($\mu g/cm^2$) |
|---|---|---|---|---|
| A | 0 | 7.5 | 32 | 20 |
| B | 0.35 | " | 14 | 10 |
| C | 0.70 | " | 8.3 | 6.1 |
| D | 1.40 | " | 5.5 | 4.7 |
| E | 2.80 | " | 4.8 | 4.0 |

As is obvious from Table 2, when the compound represented by the general formula (I) of the present invention is added to the antihalation layer, the desilvering rate remarkably increases in a manner similar to Example 1 without using a bleach accelerating bath and, consequently, bleaching time can be shortened.

EXAMPLE 3

The following layers were provided in order on a cellulose acetate film coated with a conventional subbing layer to produce a coating sample (H).

Layer-1 Antihalation layer:

The same as the Layer-1 in Example 1.

Layer-2 Intermediate layer:

The same as the Layer-2 in Example 1.

Layer-3 Red-sensitive low-speed silver halide emulsion layer:

The same as the Layer-3 in Example 1.

Layer-4 Red-sensitive medium-speed silver halide emulsion layer:

In the silver halide emulsion of the Layer-3, the following modification was carried out.

| | |
|---|---|
| Average particle size of the silver iodobromide emulsion | 0.7μ |
| Amount of the red-sensitive spectral sensitizer added | 200 cc |
| Emulsion (1) | 300 g |
| Emulsion (2) | 80 g |

The resulting silver halide emulsion was applied so as to result in a dry film thickness of 1.8μ.

Layer-5 Red-sensitive high-speed silver halide emulsion layer:

The same as the Layer-4 in Example 1.

Layer-6 Gelatin intermediate layer:

The same as the Layer-5 in Example 1.

Layer-7 Green-sensitive low-speed silver halide emulsion layer:

The same as the Layer-6 in Example 1.

Layer-8 Green-sensitive medium-speed silver halide emulsion layer:

In the silver halide emulsion layer of the Layer-8, the following modification was carried out.

| | |
|---|---|
| Average particle size of silver iodobromide emulsion | 0.7μ |
| Amount of the green-sensitive spectral sensitizer added | 170 cc |
| Emulsion (3) | 200 g |
| Emulsion (4) | 50 g |

The resulting silver halide solution was applied so as to result in a dry film thickness of 1.3μ.

Layer-9 Green-sensitive high-speed silver halide emulsion layer:

The same as the Layer-7 in Example 1.

Layer-10 Yellow colloidal silver layer:

The same as the Layer-8 in Example 1.

Layer-11 Blue-sensitive low-speed silver halide emulsion layer:

The same as the Layer-9 in Example 1.

Layer-12 Blue-sensitive medium-speed silver halide emulsion layer:

In the silver halide emulsion in the Layer-11, the following modification was carried out.

| | |
|---|---|
| Average particle size of silver iodobromide emulsion | 0.8μ |
| Emulsion (5) | 480 g |

The resulting silver halide emulsion was applied so as to result in a dry film thickness of 1.4μ.

Layer-13 Blue-sensitive high-speed silver halide emulsion layer:

The same as the Layer-10 in Example 1.

Layer-14 Gelatin protective layer:

The same as the Layer-11 in Example 1.

The sample resulting from the above is called Film (H). Aqueous solution (0.1% by weight) of Compounds (I)-(1) and (I)-(7) were added to the antihalation layer of the Film (H) in the same manner as the Film (F) in Example 1 to produce Films (I) to (L).

The Films (H) to (L) produced as described above were subjected to stepwedge exposure and the same development processing as in Example 1. After processing, the residual silver content was measured.

TABLE 3

| Film No. | Compound (I)-(1) ($mg/m^2$) | Compound (I)-(7) ($mg/m^2$) | Total Silver Content ($g/m^2$) | Residual Silver Content after Development: Bleaching for 1 Min ($\mu g/cm^2$) | Bleaching for 3 Min ($\mu g/cm^2$) |
|---|---|---|---|---|---|
| H | 0 | 0 | 9.05 | 38 | 15 |
| I | 0.70 | 0 | 9.05 | 24 | 5 |
| J | 1.41 | 0 | 9.05 | 17 | 3 |
| K | 0 | 1.08 | 9.05 | 29 | 10 |
| L | 0 | 2.17 | 9.05 | 20 | 4 |

As is obvious from Table 3, when the compounds represented by the general formula (I) of the present invention are added to the antihalation layer, the desilvering rate remarkably increases in a manner similar to Example 1 and, consequently, the bleaching time can be shortened.

While the invention has been described in detail and with reference to specific embodiments thereof, it will be apparent to one skilled in the art that various changes and modifications can be made therein without departing from the spirit and scope thereof.

What is claimed is:

1. A process for bleaching color photographic sensitive materials which comprises bleaching a silver halide color photographic sensitive material comprising a support base, a silver halide emulsion layer and a compound represented by the general formula (I) or strong acid salts thereof in a layer which does not substantially form silver salts of said compounds with a treating solution containing persulfate after being exposed to light and carrying out color development:

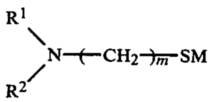

(I)

wherein M represents a hydrogen atom, an alkali metal atom, an alkaline earth metal, a quaternary ammonium group, a quaternary phosphonium group, an amidino group

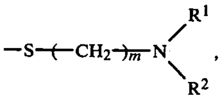

, $R^1$ and $R^2$ each represents a hydrogen atom or an aliphatic group, and m represents an integer of 2 to 4.

2. A process for bleaching color photographic sensitive materials according to claim 1, wherein said silver halide color photographic sensitive material additionally contains a compound represented by the general formula (II):

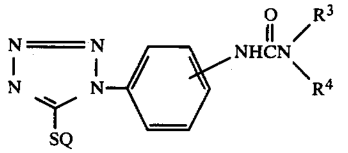

(II)

wherein Q represents a hydrogen atom, an alkali metal atom or a quaternary ammonium group, and $R^3$ and $R^4$, which may be the same or different, each represents a hydrogen atom, a nonsubstituted or substituted aliphatic group or a nonsubstituted or substituted aromatic group, and $R^3$ and $R^4$ may form a ring by bonding together.

3. A process for bleaching color photographic sensitive materials as claimed in any of claims 1 or 2, wherein the alkali metal atom is selected from the group consisting of lithium, sodium and potassium.

4. A process for bleaching color photographic sensitive materials as claimed in claim 1, wherein the alkaline earth metal is selected from the group consisting of calcium and magnesium.

5. A process for bleaching color photographic sensitive materials as claimed in claim 1, wherein the quaternary ammonium group or quaternary phosphonium group each contains up to 30 carbon atoms.

6. A process for bleaching color photographic sensitive materials as claimed in claim 1, wherein $R^1$ and $R^2$ each represents a hydrogen atom or an aliphatic group containing 1 to 30 carbon atoms.

7. A process for bleaching color photographic sensitive materials as claimed in claim 6, wherein $R^1$ and $R^2$ represent an alkyl group containing 1 to 5 carbon atoms.

8. A process for bleaching color photographic sensitive materials as claimed in any of claims 1 or 2, wherein the compound represented by the general formula (I) is present in an amount of $1\times10^{-7}$ mol to $1\times10^{-3}$ mol per square meter of the photographic sensitive material.

9. A process for bleaching color photographic sensitive materials as claimed in claim 8, wherein the compound represented by the general formula (I) is present in an amount of $1\times10^{-6}$ mol to $1\times10^{-4}$ mol per square meter of the photographic sensitive material.

10. A process for bleaching color photographic sensitive materials as claimed in claim 2, wherein $R^3$ and $R^4$ each represents an alkyl or alkenyl group having 18 or less carbon atoms.

11. A process for bleaching color photographic sensitive materials as claimed in claim 2, wherein $R^3$ and $R^4$ each represents an aryl group containing 6 to 20 carbon atoms.

12. A process for bleaching color photographic sensitive materials as claimed in claim 2, wherein the compound represented by the general formula (II) is present in an amount of $1\times10^{-2}$ mol to 100 mols per mol of silver.

13. A process for bleaching color photographic sensitive materials as claimed in claim 12, wherein the compound represented by the general formula (II) is present in an amount of $1\times10^{-1}$ mol to 10 mols per mol of silver.

14. A process for bleaching color photographic sensitive materials as claimed in any of claims 1 or 2, wherein the bleaching is carried out utilizing bleaching solution containing persulfates as the bleaching agent.

15. A process for bleaching color photographic sensitive materials as claimed in claim 14, wherein the persulfate bleaching agents are selected from the group of agents consisting of potassium persulfate, sodium persulfate and ammonium persulfate.

16. A process for bleaching color photographic sensitive materials as claimed in any of claims 1 or 2, wherein the bleaching is carried out utilizing a bleaching solution having a pH within the range of from 1 to 7.

17. A process for bleaching color photographic sensitive materials as claimed in claim 16, wherein the pH of the bleaching solution is within the range of from 1.5 to 3.5.

18. A silver halide color photographic sensitive material, comprising:

a support base;

a silver halide emulsion layer on the support base; and a compound represented by the general formula (I) or a strong acid salt thereof:

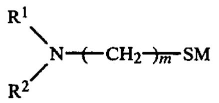

(I)

wherein M represents a hydrogen atom, an alkali metal atom, an alkaline earth metal, a quaternary ammonium group, a quaternary phosphonium group, an amidino group or

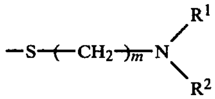

, $R^1$ and $R^2$ each represents a hydrogen atom or an aliphatic group, and m represents an integer of 2 to 4.

* * * * *